(12) United States Patent
Genest (10) Patent No.: US 6,741,728 B1
(45) Date of Patent: May 25, 2004

(54) FOOTWEAR SIZING DATABASE METHOD

(75) Inventor: Leonard J. Genest, Santa Ana, CA (US)

(73) Assignee: Footechnology Partners LLC, Irvine, CA (US)

( * ) Notice: Subject to any disclaimer, the term of this patent is extended or adjusted under 35 U.S.C. 154(b) by 697 days.

(21) Appl. No.: 09/624,822

(22) Filed: Jul. 25, 2000

(51) Int. Cl.[7] ................................................. G06K 9/00
(52) U.S. Cl. ...................................... 382/115; 382/285
(58) Field of Search ................................. 382/100, 106, 382/115, 199, 194, 203, 154, 285, 286, 305; 702/152, 153, 159; 700/130, 129, 131, 134, 135; 705/26, 27; 600/592; 33/3 R, 4–5, 3 C; 12/133 R, 146 L; 250/559.19–559.24

(56) References Cited

U.S. PATENT DOCUMENTS

| 5,195,030 A | * | 3/1993 | White ........................ 705/26 |
| 5,231,723 A | * | 8/1993 | White et al. ............... 12/133 R |
| 6,029,358 A | * | 2/2000 | Mathiasmeier et al. ....... 33/3 R |
| 6,289,107 B1 | * | 9/2001 | Borchers et al. ............ 382/100 |
| 6,546,356 B1 | * | 4/2003 | Genest ........................ 702/153 |
| 6,549,639 B1 | * | 4/2003 | Genest ........................ 382/100 |

* cited by examiner

*Primary Examiner*—Leo Boudreau
*Assistant Examiner*—Ishrat Sherali
(74) *Attorney, Agent, or Firm*—Derrick Michael Reid (57) ABSTRACT

A footwear database system receives precision three dimensional foot image data of imaged feet of human beings, and receives precision footlast 3D image data from footwear manufacturers for storage into databases for automatic determination of footwear sizes. After imaging feet and storing the footlast data, a customer can thereafter remotely select, for example, through catalogs and web sites, a style of footwear and the footwear database system then determines the acceptable and best fitting size for the desired style of the footwear of a respective footwear manufacturer, and in so doing provides an automatic best fitting size selection for reducing footwear returns due to poor and uncomfortable fits.

17 Claims, 5 Drawing Sheets

FOOTWARE SIZE DETERMINATION PROCESS

FIG.1A FOOTWARE PROCUREMENT SYSTEM

FIG.1B FOOTWARE SIZE DETERMINATION PROCESS

FIG. 2A FOOT PROFILE

FIG. 2B FOOT PRINT

| FOOT LENGTH Y | MEDIAL WIDTH XM | LATERAL WIDTH XL | INSTEP HEIGHT ZI | ARCH HEIGHT ZA |
|---|---|---|---|---|
| Y1 | XM1 | XL1 | ZI1 | ZA1 |
| Y2 | XM2 | XL2 | ZI2 | ZA2 |
| Y3 | XM3 | XL3 | ZI3 | ZA3 |
| Y4 | XM4 | XL4 | ZI4 | ZA4 |
| Y5 | XM5 | XL5 | ZI5 | ZA5 |
| Y6 | XM6 | XL6 | ZI6 | ZA6 |
| ⋮ | ⋮ | ⋮ | ⋮ | ⋮ |
| Yn | XMn | XLn | ZIn | ZAn |

FIG. 3A FOOT DATA COORDINATES

| FIT | LEFT FOOT | RIGHT FOOT |
|---|---|---|
| FIT - ID | +Yn  +XMn  +XLn  +ZIn  +ZAn<br>−Yn  −XMn  −XLn  −ZIn  −ZAn<br>WYn  WXMn  WXLn  WZIn  WZAn | +Yn  +XMn  +XLn  +ZIn  +ZAn<br>−Yn  −XMn  −XLn  −ZIn  −ZAn<br>WYn  WXMn  WXLn  WZIn  WZAn |

FIG. 3B FIT DATA STRUCTURE

| HUMAN | LEFT FOOT | RIGHT FOOT |
|---|---|---|
| HUMAN-ID | Yn  XMn  XLn  ZIn  ZAn | Yn  XMn  XLn  ZIn  ZAn |

FIG. 3C HUMAN FEET IMAGE DATA STRUCTURE

| LAST | LEFT FOOT | RIGHT FOOT |
|---|---|---|
| LAST-ID | Yn  XMn  XLn  ZIn  ZAn | Yn  XMn  XLn  ZIn  ZAn |

FIG. 3D FOOTLAST DATA STRUCTURE

| MFG - ID | STYLE - ID | LAST - ID | FITTING - ID |
|---|---|---|---|

FIG. 4A FOOTWARE DATA STRUCTURE

| MFG - 1 | STYLE - 1 | LAST - 1 | FITTING - 1 |
|---|---|---|---|
| MFG - 1 | STYLE - 1 | LAST - 2 | FITTING - 2 |
| MFG - 1 | STYLE - 1 | LAST - 3 | FITTING - 2 |
| MFG - 1 | STYLE - 1 | LAST - 4 | FITTING - 3 |
| MFG - 1 | STYLE - 2 | LAST - 5 | FITTING - 6 |
| MFG - 1 | STYLE - 2 | LAST - 3 | FITTING - 7 |
| MFG - 1 | STYLE - 2 | LAST - 6 | FITTING - 2 |
| MFG - 2 | STYLE - 3 | LAST - 7 | FITTING - 8 |
| MFG - 2 | STYLE - 3 | LAST - 3 | FITTING - 7 |
| MFG - 2 | STYLE - 4 | LAST - 8 | FITTING - 7 |
| ⋮ | ⋮ | ⋮ | ⋮ |
| MFG - 3 | STYLE - 5 | LAST - 9 | FITTING - 9 |

FIG. 4B FOOTWARE DATABASE

FOOTWEAR SIZING DATABASE METHOD

REFERENCE TO RELATED APPLICATION

The present application is related to applicant's copending application entitled "Body Part Imaging System" Ser. No. 09/562,842, filed May 1, 2000, by the same inventor.

The present application is related to applicant's copending application entitled "Body Part Imaging Method" Ser. No. 09/562,843 May 1, 2000, by the same inventor.

FIELD OF THE INVENTION

The invention relates to the field of footwear imaging and sizing. More particularly, the present invention relates to imaging of human feet and footwear sizing database management.

Incorporation By Reference

The present application here incorporates by this reference applicant's copending application entitled "Body Part Imaging System" Ser. No. 09,562,842, filed May 1, 2000, by the same inventor, and applicant's copending application entitled "Body Part Imaging Method" Ser. No. 09/562,843 May 1, 2000, by the same inventor. These prior applications disclose and teach systems and methods for imaging of feet for providing foot measured dimensions well suited for use in the present invention.

BACKGROUND OF THE INVENTION

Footwear retailers and manufacturers seek to provide means of fitting footwear to feet of human beings. The fit should be proper and comfortable. Typically, a customer would purchase footwear from a retailer only after trying on the footwear in the store, after selection and tying on several pairs of footwear, such as shoes or boots, of a particular style. Beside retail store sales, catalogs have also been used to indirectly procure footwear. The advent of wide spread Internet communications has enabled purchasers to conveniently and indirectly procure desired products without having to travel to a specific in-store retailer. As with catalog purchasers, they're is no way for the customer to try on the pair of footwear to verify proper and comfortable fitting prior to ordering the footwear through an Internet web site or from a catalog. Consequently and often, indirectly purchased footwear through catalogs and the Internet do not fit properly and comfortably when received and the footwear items are often returned scuffed or worn. Even when a customer orders the correct designated size of footwear through indirect channels of trade, variants in footwear sizing leads to poor fitting and uncomfortable footwear that are returned or scraped. The footwear industry return rate for improper fitting or uncomfortable footwear may exceed two billion dollars per year in the United States alone. The advent of a precision fitting method could save the footwear industry billions in lost sales and hundreds of millions of dollars per year in write-offs for scrapped product that cannot be reclaimed.

Footwear manufactures often provide purchasers with a wide selection of styles of footwear from which to choose. The footwear is typically manufactured on footwear lasts, referred to herein as footlasts that define the inside cavity of the footwear. The materials that comprise footwear are wrapped, nailed or glued around the footlast that acts as a fixture or mold to construct the footwear. Hence, the footwear footlasts defines the inside cavity of footwear. To provide a complete selection of various sizes from small to large sizes, in various lengths and widths, the manufactures uses a corresponding set of various sized footlasts to manufacture a style of footwear in ranges of sizes. The cavity of the footwear is a three dimensional cavity defined by the footwear footlasts. Because different footwear manufacturers use different footlasts for their respective styles and sizes, often a footlast of a designated size will be substantially different from the same designated size of a corresponding footlast of a different style. Even though the manufacturer may designate a size, that size, defined by the footlast cavity is not precise disadvantageously leading to nonconforming standard sized shoes incorrectly at times referenced to standard designated sizes. Additionally, the size and shape of human feet vary greatly from one human to another. Often, feet of the same standard size are substantially different in shape leading often to poorly fitting footwear of the same but presumed correct designated size. With differently shaped and sized footlasts used to make footwear for purchasers having differently shaped feet, often footwear purchased of the correct designated size will not properly comfortably fit. The variation in sizes between feet and footlasts of the same designated sizes leads to large return rates when the customer can try on footwear and even greater returns when the customer cannot try on the footwear. Furthermore, because the sets of footlasts for respective styles vary greatly between styles as well, the selected style, selected designated size, and individual shaped feet do not provide a customer with certainty of procuring properly fitting footwear without trying on the shoes in the retail store to attempt verify a proper fit prior to purchase.

To complicate the imprecision of footwear selection, different styles have different shapes that lead to different fits for the same designated size for the same pair of feet. Some areas of the foot and the corresponding locations within the cavity of the footwear are more critical than other locations depending on the style of footwear selected. For example, the width fit in stiff footwear, such as dress shoes, is more critical than the width fit in soft-shoes, such as comfort walking shoes. With a large variation between footlasts, styles, and feet, often the selection of the footwear is imprecise leading to many returns. Consequently, customers often reframe from purchasing footwear for themselves as well as for others resulting is missed sale opportunities for the customers and manufactures. The majority of footwear returns from both direct in-store and indirect non-store are first for fit then for comfort. Proper length and width sizing of the inside of footwear to the length and width of feet does not assure that the best size of that style with a comfortable fit is selected. The sizes for different styles and from different manufacturers may require size variations of up to two sizes using the same American footwear scale for size designation. The ordering of a correct designated size does not guaranty that the footwear will properly and conformably fit.

It is now possible to image a human foot in traditional X-Y-Z three dimensions with accurate precision. A foot can be accurately imaged using optical scanning systems and methods. To image the foot, that customer may be provided an identification number for referencing the foot image to the respective human. However, because there is no current practical way to precisely match the shape of a foot to a corresponding style and footlast, the three-dimension foot image and identification is of little value when selecting footwear. These and other disadvantages are solve or reduced using the present invention.

SUMMARY OF THE INVENTION

An object of the invention is to provide a system and method for precise selection of proper and comfortable fitting footwear.

Another object of the invention is to provide a system and method for matching foot images to footlasts for precise selection of proper and comfortable fitting footwear.

Yet another object of the invention is to provide a system and method for matching foot images to footlasts using fitting tolerances for precise selection of proper and comfortable fitting footwear.

Still another object of the invention is a system and method for matching foot images to respective footlasts within respective fitting tolerances and weighted comfort zones for precise selection of proper and comfortable fitting footwear.

Still a further object of the invention is a system and method for matching precision foot images to respective precision footlasts of respective footwear styles within respective fitting tolerances and weighted comfort zones for precise selection of proper and comfortable fitting footwear.

The invention is directed to a comprehensive precision system and method for matching precision foot images to respective precision footlasts of respective footwear styles for precise selection of proper and comfortable fitting footwear. A proper fit goes to correct sizing while a comfortable fits goes to the feel of the footwear when worn. The system is enhanced using respective fitting tolerances and weighted comfort zones for improved precision in footwear selection. Three-dimensional (3D) images of feet are matched to three-dimensional images of footlasts. Computer database storage and processing enables the matching of foot images with correctly sized footlasts that defines the cavity of the footwear. Because both the feet and shoe cavities are precisely imaged in 3D, the customer can select footwear with a high degree of confidence that the selected style and size of the footwear will properly and comfortably fit the feet when received.

The human feet are imaged and crossed referenced to a customer identification number (ID). The foot images are represented in a precision 3D-foot data structure. The footlasts that define the inside cavity are cross-referenced to particular styles and manufacturers. The footlast are also represented in a precision 3D-foot data structure. In the preferred form, the footlast and foot image 3D data structure are the same for ease of matching foot images to the best proper and comfortable fitting footwear. After imaging the feet of a human being and imaging the footlast, a customer can at any time provide the customer ID and the desired style of a manufacturer. The system and method cross-references the customer ID to the 3D-foot image representation. Then the system and method selects among the sets of 3D footlast representations to automatically match the foot image to the best footlast from a set of footlasts for the selected style and present the human with the best fit size.

In the preferred form, a fitting database is used to provide enhanced selection of the best footlast for the selected style and foot image. The fitting database has a plurality of fittings parameters each of which defines in whole or in part an imaginary 3D shell disposed in computer relation between the exterior of the foot defined by the foot images and the interior of the footwear cavity defined by the footlast. The footlast fittings have a similar data structure as the foot images where each has a plurality of X-Y-Z coordinate positions. Groups of contiguous interior cavity coordinates may be grouped into comfort zones for ease of calculation. Each footlast coordinate position in each zone uses the same set of fitting data between respective positions with reference to the feet. The fitting data is effectively combined with the footlasts to provide the tolerance shell about the footlast image. When the foot image coordinate positions fall within the respective fitting tolerances of the respective footlast, then the fit is deemed proper. When the footlast fitting tolerances are such that a plurality of footlast are deemed proper and comfortable, the zones can be weighed to select the best fitting footlasts from the plurality of acceptable footlast. The best fitting footlast corresponds to a particular size of footwear for the selected style. The customer may then procure the footwear with a high degree of confidence that the selected recommended footlast size will fit proper and comfortable, thereby minimizing footwear returns. These and other advantages will become more apparent from the following detailed description of the preferred embodiment.

DETAILED DESCRIPTION OF THE PREFERRED EMBODIMENT

Figure 1A:
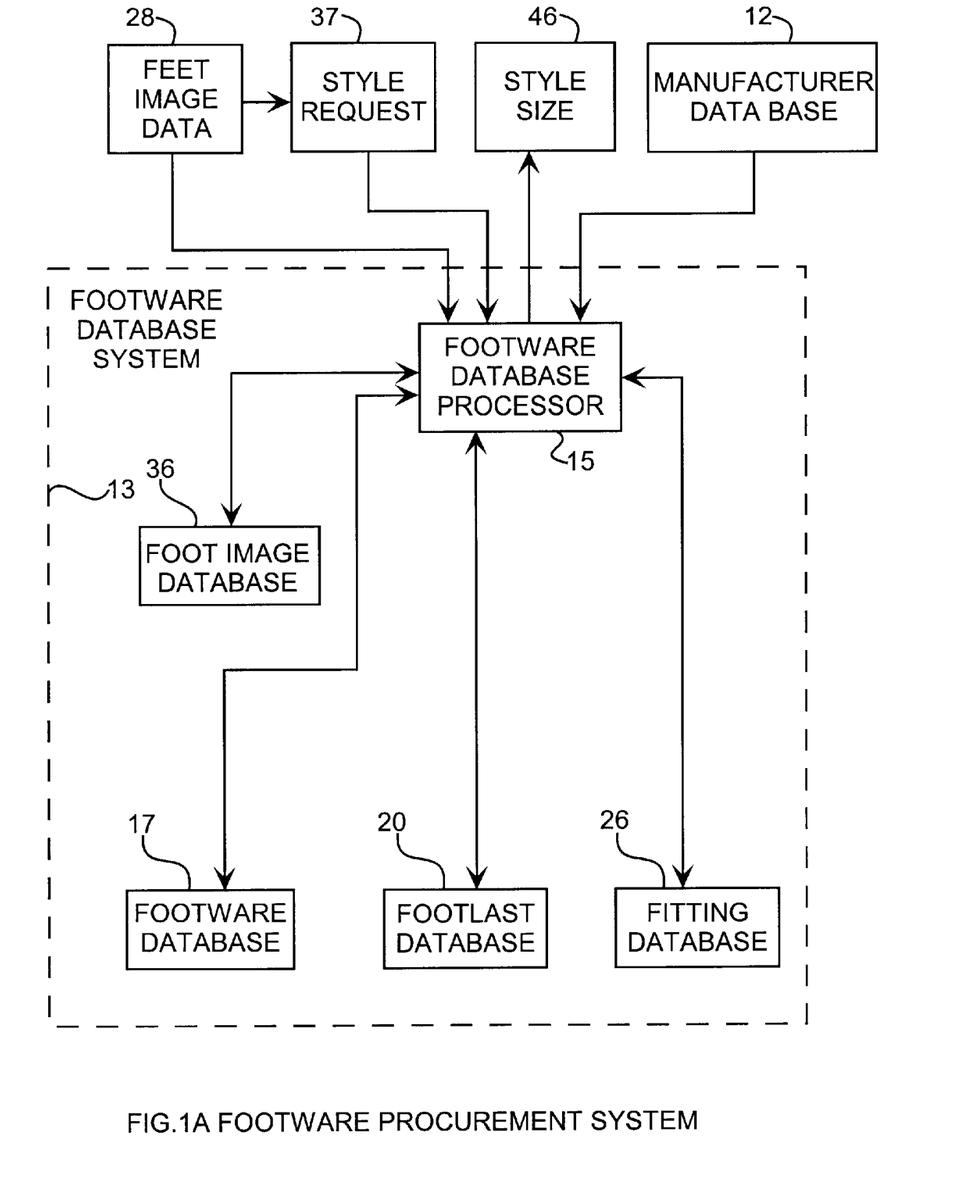
FIG. 1A is a block diagram of a footwear procurement system.
Figure 1B:
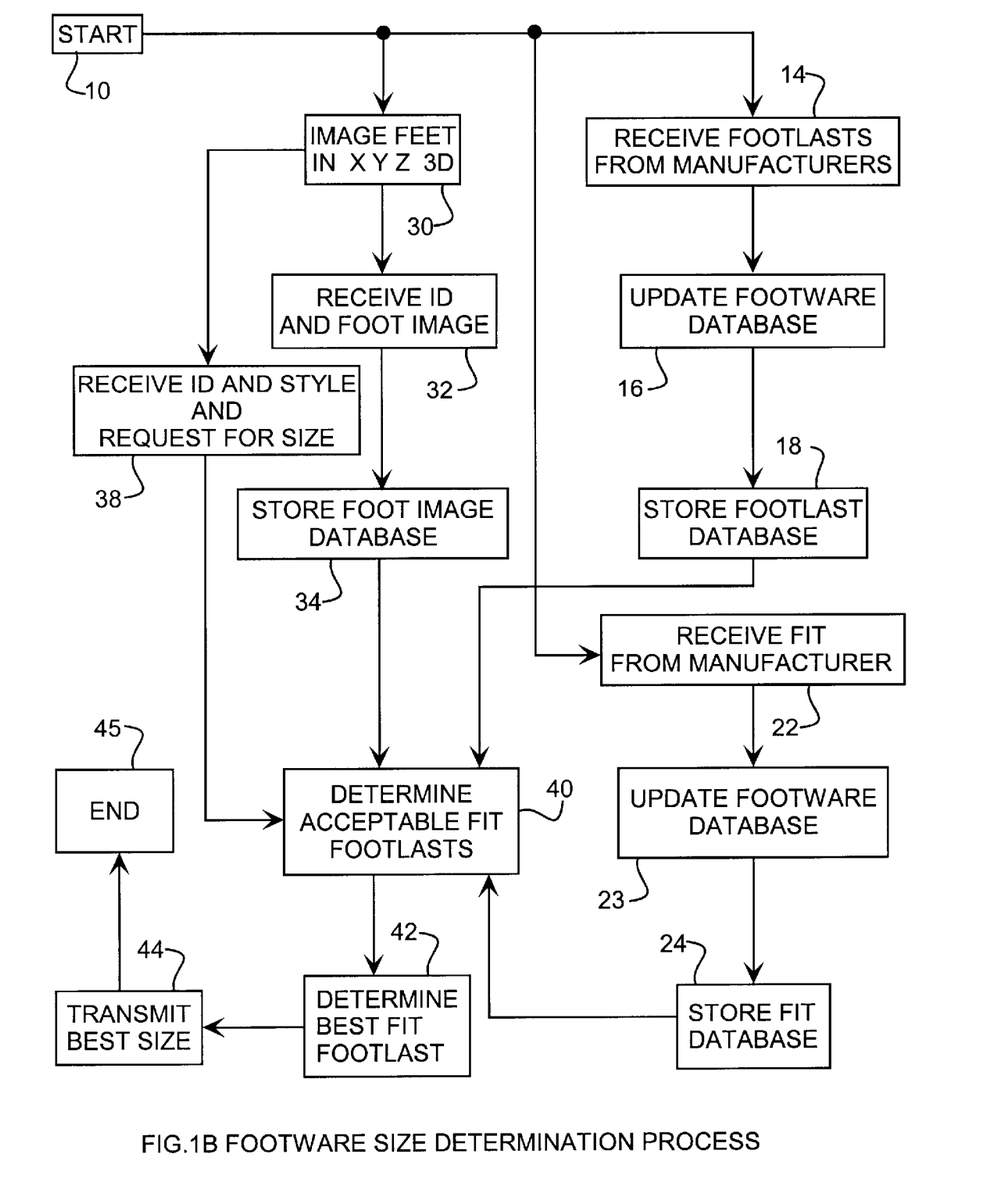
FIG. 1B is a flow chart of a footwear size determination process

An embodiment of the invention is described with reference to the figures using reference designations as shown in the figures. Referring to FIGS. 1A and 1B, the footwear selection process starts 10 with a preexisting manufacturer database 12 that is created by one or more manufacturers and communicated to a remote footwear database system 13 that receives 14 footlast data through a footwear database processor 15 that in turn updates 16 a footwear database 17 for referencing the received footlast data 14 to the respective footwear style of a respective manufacturer. The footlasts dimensional data is stored 18 in a footlast database 20. The footlasts may be imaged into footlast data using optical scanning systems and methods. The manufacturer database 12 may further include fitting data that is received 22 for updating 23 the footwear database 17 for cross referencing the fitting data to the respective footlast, style and manufacturer. The fitting data is typically generated by the respective manufacturer having expert design knowledge of how manufactured styled footwear fit human feet of differing shapes and sizes for providing proper and comfortable fits. The fitting data is stored 24 in a fitting database 26. The fitting data and footlast data is preferably three dimensional 3D data for defining the inside cavity of a footlast of a particular style and for defining a 3D tolerance shell that provides zone weighted tolerances sizing of a footlast to a foot, respectively. The manufacturer, style, footlast and fitting preferably all have respective identifications for cross-referencing.

A pair of human feet are imaged 30 in 3D generating foot image data 28 that is communicated to the footwear database system 13. The foot image data is cross-referenced to the respective human being preferably using a human identification. Preferably, the foot image 3D data includes an identification (ID) that is imaged, for example, as a bar code, along with the feet during the imaging process so that the 3D foot image data is inherently cross referenced to the respective human being. The foot image data is received 32 and stored 34 in a foot image database 36. After imaging the foot into imaged foot 3D data, after imaging a set of footlast into a set of footlast 3D data, and after generating 3D fitting data, a customer may then request 36 a desired style of footwear while providing the customer human ID. The request 36 is received 38 and the footwear database processor 15 then determines which ones of the set of footlasts for the requested style have acceptable fitting. Generally, the fitting data is combined with the footlast data and then compared to the foot image data to determine 40 which ones, if any, of the footlasts for the requested styles are acceptable. When more than one footlast of the set of footlasts for the requested style is acceptable, the footwear database processor determines 42 which one of the acceptable footlasts is the best fitting footlast. The footwear database system then transmits 44 the identification of the best fitting footlast as a style size 46 to end 45 the automated precise footlast determination process. The customer can then order this correct size for the requested style from the manufacturer without having first tried on the footwear for proper and comfortable fit verification. At any later time, a customer need only provide the style and manufacturer of footwear desired and the identification of the imaged feet to the footwear data system to select the best fitting footlast, and its reported size. In this manner, the selection process becomes automated. The precision of the 3D images, footlasts and fittings enable automatic selection of the best fitting size for the desired style without the advance trying on of footwear for pre-purchase fit verification. In this manner, customers are now free to indirectly procure footwear with a high degree of confidence that the procured footwear with properly and comfortably fit when received. The system and method thus enables remote precision selection of footwear well-suited for indirect procurement of personal and gift footwear for the public.

Figure 2A:
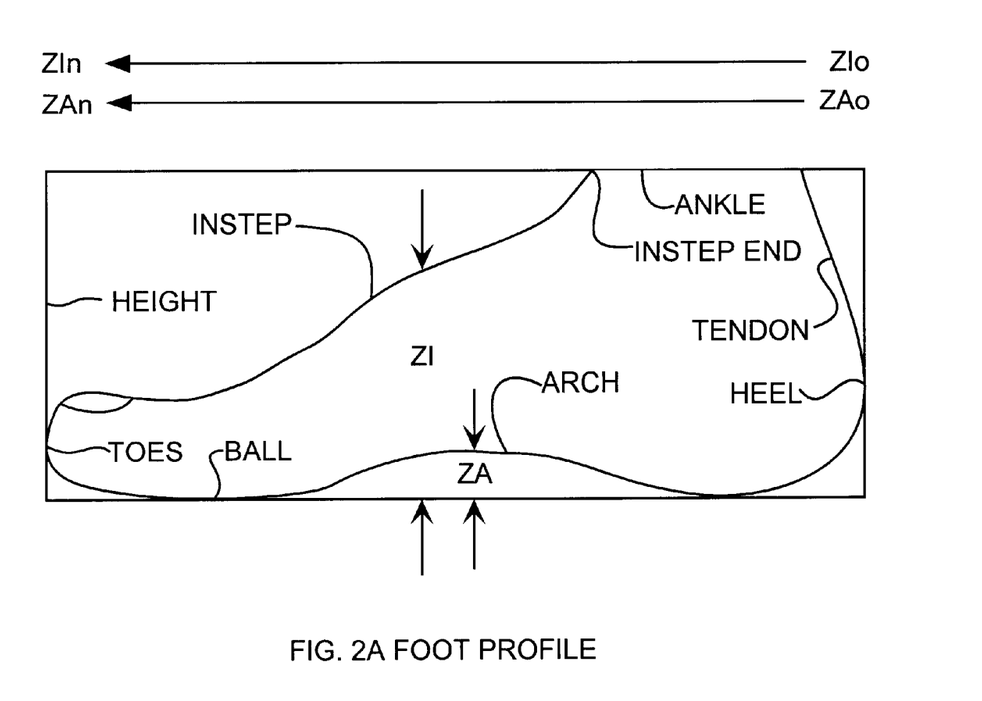
FIG. 2A depicts an imaged foot outline in Y-X coordinates.
Figure 2B:
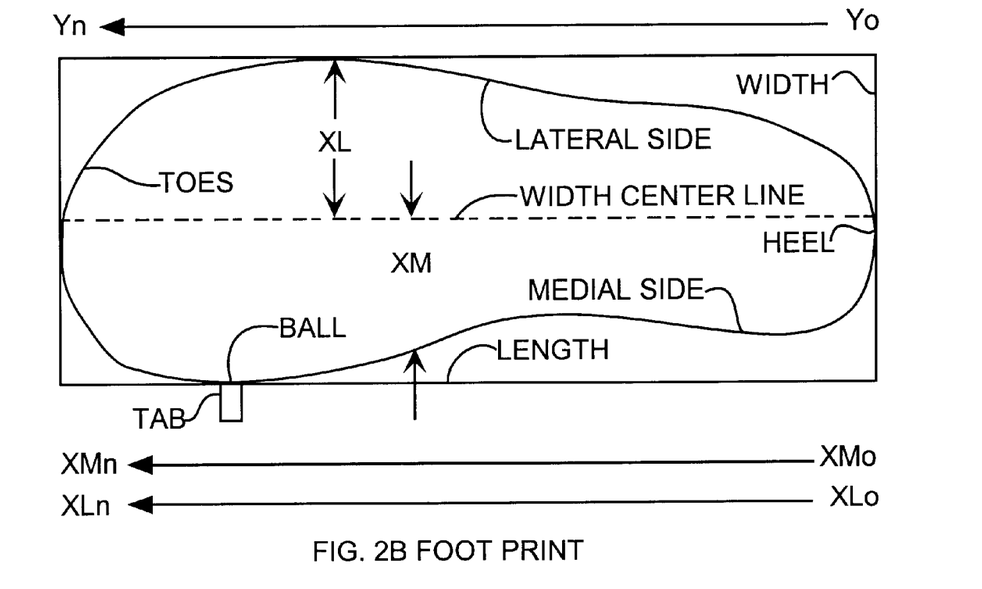
FIG. 2B depicts an imaged foot profile in Y-Z coordinates.
Figure 3A:
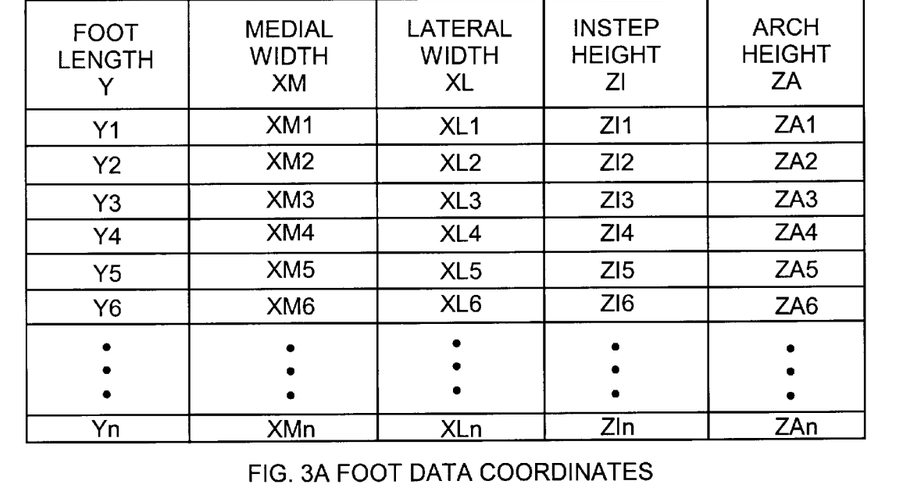
FIG. 3A depicts a foot data coordinate system.
Figure 3B:
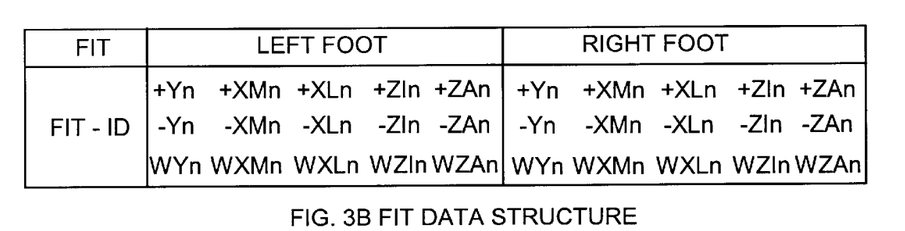
FIG. 3B depicts a Fit data structure.
Figure 3C:
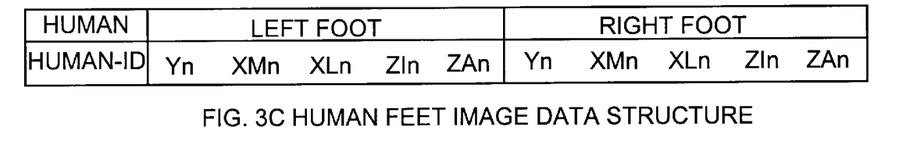
FIG. 3C depicts a foot image data structure.
Figure 3D:
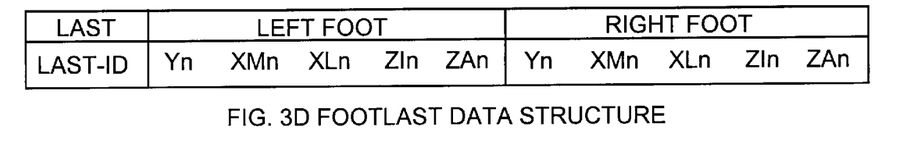
FIG. 3D depicts a footlast data structure.

Referring to FIGS. 2A and 2B, a human foot is imaged in 3D. There are many possible ways in which to represent a 3D image. In the preferred form, the 3D foot image comprises a two-dimensional (2D) footprint (top view outside foot edge) and a side view 2D foot profile that when correlated together provide a 3D image of the foot. The foot print and foot profile are defined by an X-Y-Z 3D coordinate system well suited for representing profile and footprint images within rectangular boxes defined by the coordinate system. The profile view depicts the toes, ball, arch, instep, ankle, tendon and heel of the foot while the footprint view depicts toes, ball, lateral side, medial side and heel of the foot. In the preferred form, the footprint includes Y coordinates Y0 through Yn extending the length of the foot. The length of the foot is divided into a predetermined number segments, for example 32 segments for referencing the Yn dimension, for example, between Y0 and Y32. The Xn width and Zn height dimension are referenced to the segments so that the Yn length, Xn width and Zn height data are conveniently correlated to the common X-Y-Z coordinate system.

The width of the foot is referenced to X coordinates extending the maximum width of the foot. The X coordinates are preferably divided into the lateral XL and medial XM dimensions respecting the width centerline extending the length of the foot through the center of the foot print. The X coordinates XM0 and XL0 respectively through XMn and XLn extend from the centerline to the medial and lateral sides of the foot, respectively. The Z coordinates are divided into instep height ZI extending vertically in height from ZI0 through ZIn, and the arch height ZA extending vertically in height from ZA0 through ZAn. In combination, Yn dimension defines the length heel-to-toe of the foot, XMn dimensions define the medial side of the foot heel-to-toe, XLn dimensions define the lateral side of the foot heel-to-toe, ZIn dimensions define the top of the foot including instep, ankle and tendon portions, and ZAn dimensions define the bottom of the foot from heel to toe. In the ankle portion where the leg extends vertically from the foot, an instep end point is determined. Preferably, the foot imaging system is modified to determined the end point which may be determined, for example, where the height rate of change dZ/dy exceeds a predetermined instep slope value, at which point, the foot profile has a maximum height for truncating the ankle portion to that maximum height. In this manner, the footprint and foot profile offer an X-Y-Z coordinate system for defining the 3D foot image adequately for footwear fitting. In a particular improvement, the footprint image may be enhanced to include a ball tab that marks the ball of the foot for accurate fitting of the bending of the footwear respecting the bending of the foot when wearing the footwear. The tab can be recognized by computer processing which recognizes the shape of the tab abutting the edge of the foot on the medial side and marks the ball location. Positing the foot relative to a tab marker during foot optical imaging can also create the tab image and determine its position. Alternatively, and tab may be simply temporarily affixed to and extending outwardly from the ball of the foot during imaging.

Referring to FIGS. 1A through 3D, and more particularly to FIGS. 3A, 3B, 3C and 3D, the 3D foot image of a pair feet is defined by a human foot image data structure having the human ID, left foot dimensions and right foot dimensions. The left and right foot dimensions are represented within the foot data X-Y-Z coordinate system comprising the Yn, XMn, XLn, ZIn and ZIn coordinate points having respective X-Y-Z dimensions. In order to compare a foot image to the footlast data, which is also a 3D image of the footlast, the foot data is also preferably stored using the same coordinate systems defined by the footlast data structure having a footlast ID, left foot dimensions and right foot dimensions. Hence, for ease of computation, the foot image data and footlast image data having the same data structure using the same coordinate system. In order to determine the best fitting footlast, the fitting data is also preferably stored using a similar data structure referencing the same coordinate system. While there are many possible ways of determining the best fit, the preferred form Uses +/– fit tolerances +Yn, +XMn, +XLn, +ZIn, +ZAn, –Yn, –XMn, –XLn, –ZIn and –ZAn and respective weights WYn, WXMn, WYLn, WZIn and WZIn. The +/– tolerances and weight are preferably completely defined, but a partial set of tolerance and weight may be used as well for determining the fit to only a few critical conform zones about the foot.

Figure 4A:
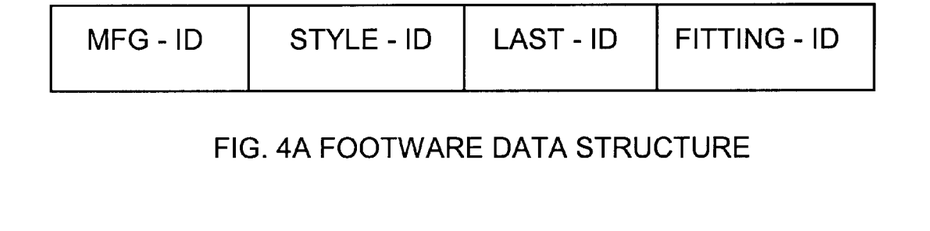
FIG. 4A depicts a footwear data structure.
Figure 4B:
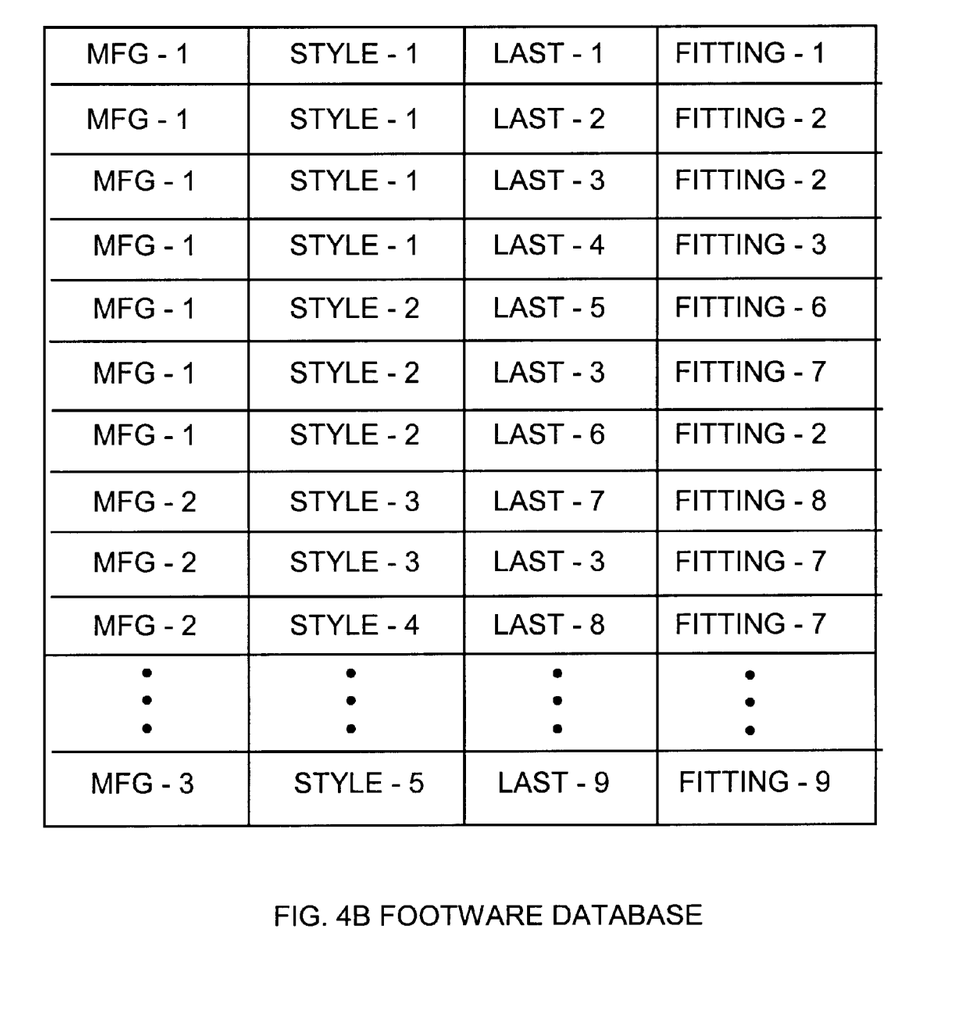
FIG. 4B depicts a footwear database.

Referring to all of the Figures, and more particularly to FIGS. 4A and 4B, each manufacture may provide data for constructing the footwear database using a footwear data structure comprising a manufacturer ID, style ID, footlast ID and fitting ID. The manufacturer ID cross-references a respective manufacturer within the footwear database. The style ID cross-references a respective style within the footwear database. The footwear database cross references the manufacturers and styles to respective footlast and fittings by respective IDs. The footlast ID cross-reference a respective footlast record within the footlast database. The fitting ID cross-references a respective fitting record within the fitting database. As may be apparent, some footlast records may be used for different styles; for example, footlast 3 is used for styles 1, 2 and 3 where styles 2 and 3 are for different manufacturers 1 and 2. As may be apparent some fitting records may be used for different footlasts; for example, fitting 2 is used for footlast 2 and 6. Hence, the footwear database enables the use of the same footlast and fitting data records for differing styles.

The determination of acceptable and best fits may be had using a vast variety of fitting algorithms. These algorithms may be specified by the manufacturer having expert knowledge of the manner by which their respective footwear tend to fit variously shaped and sized human feet. By way of example, a relatively simple exemplar algorithm may be used. In the exemplar algorithm, the coordinate system is used to determine when a coordinate point of a foot images is within the footlast tolerances defined by the combination of the footlast dimensions and the +/− tolerances. The +/− tolerances provide a dimensional range. The two +/− tolerance values can be either positive for clearances or negative for interference. For example, the tolerance could be +15 mm and −5 mm, meaning that up to 15 mm of clearance to 5 mm of interference. Clearances provide comfort space between the foot and footwear whereas interference provides an overlapping fit between the foot and footwear, at the respective coordinate points within a zone. For example, up to 15 mm of toe clearance is desirable for stiff dress shoes but certainly not less then 6 mm. Some shoes stretch and use elastic type materials and conformable fits or stretching of the footwear material may require interference for the best fit. The +/− tolerance are used in ranges, both extremes of the range may be clearance positive values, may be two interference negative values or may be a clearance to an interference value. The exemplar algorithm compares respective foot image dimensions to respective footlast dimension combined with respective fitting tolerances all of which are cross referenced to each other for each coordinate point using the coordinate system. By way of example, the width is a critical comfort zone, may be imaged to be 130 mm, with the style selected has three footlasts, size C at 110 mm, size D at 120 mm and size E at 130 mm in respectively C, D and E footlast for the desired footwear style. The tolerances for each C, D and E fitting are, in the exemplar form, the same for all three sizes, and are by way of example, +15 mm and −5 mm. The determination of an acceptable fit compares the 130 mm of the foot image to size C at 110 mm+15 mm/−5 mm, size D at 120 mm +15 mm/−5 mm and size E at 130 mm +15 mm/−5 mm. In the case of size C, the 130 mm foot image width is outside the acceptable range between of 125 mm and 105 mm. In the case of sized D and E, the 130 mm foot image width is within the 135 mm to 115 mm range and 145 mm to 125 mm range. Hence, size C is unacceptable and sizes E and D are acceptable. In this manner, comparing image dimensions to ranges defined by the footlast dimensions and fitting tolerances, each coordinate point can be compare to determine that all of the coordinate points are acceptable to determine if the footlast has an acceptable size.

In the case of determining that, for a given style, there is a plurality of acceptable sized footlasts, the process in further enhanced to determine which one of the acceptable sized footlast is the best footlast. As with the determination of an acceptable fit, the best-fit determination can be accomplished by any of a vast variety of algorithms. By way of example, an exemplar best-fit algorithm is used. In the exemplar algorithm, each coordinate point is assigned a zero or one coordinate value depending on whether the foot image dimension is less than or is greater than or equal to the footlast dimension. The coordinate fit value for each coordinate point is then multiplied by a respective weight, that may for example, be a value between one and ten providing respective fit products that are summed together into an overall fit value. The acceptable footlast providing the highest fit value is deemed to be the best fit value. By way of example, only three coordinate points, the toe length point Y31, the ball point XM25 and instep point ZI20 are specified and used to determine the best fit. The weight WY31, ZI20 and WXM25 are respectively 8, 4, and 6. In the case of the D size, for example, the coordinate values are respectively 0, 0, and 1 and for the E size, 1, 1, and 0. The fit value for the D size is then 8×0+4×0+6×1=6, and the fit value for the E size is 8×1+4×1+6×0=12. Hence, using this algorithm, the E size is determined to be the best fitting of the acceptable D and E sized footlasts.

While the above data structures, databases, coordinate system and calculations can be of many various forms, in general, the foot is imaged in 3D and then compare to a 3D footlast image. The comparison is preferably done point by point in a coordinate system that offers great precision is specifying the extent of the fit. The comparison may be enhanced by zone tolerances and zone weight tolerances to determine acceptable and best fitting footlast. By way of example of an enhancement, a group of coordinate points can be grouped together as a comfort zone. For example, XM23-XM26 can be the medial side of the foot ball zone. In this zone, the tolerances and weight may be identical, so that only one value of tolerance and weight need be stored for all coordinates in that zone. For another example, the Y0-32 length dimension coordinates need not be stored because the Y32 heel-to-toe length is stored and the actual Y1-32 coordinate values can be easily computed when needed to reduce database storage requirements. Furthermore, the dimensional values can be quantized into integer values for ease of computer processing. There are a wide variety of data compression algorithms that can be used, but fundamentally, the system and method compares 3D foot images to 3D footlast representations for automatic fit determination using one or more tolerances. Those skilled in the art can make enhancements, improvements, and modifications to the invention and these enhancements, improvements, and modifications may nonetheless fall within the spirit and scope of the following claims.

What is claimed is:

1. A method for determining an acceptable fit of a desired style of footware in reference to footlasts defining respective sizes of the desired style of footware, the method comprising the steps of, storing a three dimensional (3D) foot image representation defining an exterior contour of a human foot, storing respective 3D footlast representations defining respective interior contours of the footlasts, and determining which one or more of the footlasts has an acceptable fit when one or more respective ones of the interior contours fits about the exterior contour, wherein, the 3D foot image representation provides foot image dimensions referenced to respective 3D coordinates in a 3D coordinate system, the 3D footlast representations provide footlast dimensions referenced to the respective 3D coordinates, and the determining step determines when one or more footlast dimensions fits about respective foot image dimensions at the respective 3D coordinates.

2. The method of claim 1 wherein, 3D foot image representation and the 3D footlast representations have identical contour data structures during the foot image storing step and footlast storing step for referencing the 3D image representation and the 3D footlast representations to the 3D coordinate system.

3. The method of claim 1 further comprising the step of, storing at least one fitting representation for providing tolerances of the 3D footlast representations, one of the 3D footlast representations fits about the 3D foot image representation when the exterior contour is within interior contour combined with the tolerances.

4. The method of claim 3 wherein, 3D foot image representation and the 3D footlast representations have an identical contour data structure during the foot image storing steps and footlast storing step, the identical contour data structure defining a 3D coordinate system, and the fitting representation is a 3D fitting representation, 3D fitting representation having a fitting data structure for referencing the tolerances to the 3D coordinate system.

5. The method of claim 1 wherein, the 3D foot image representation provides foot image dimensions referenced to respective 3D coordinates, the foot image representation has length dimensions for respective Yn coordinates, medial width dimensions for respective XMn coordinates, lateral width dimensions for respective XLn coordinates, instep height dimensions for respective ZIn coordinates and arch height dimensions for respective ZAn coordinates, the Yn, XMn, XLn, ZIn and ZAn coordinates forming the 3D coordinate system, the 3D footlast representations provide footlast dimensions referenced to the respective 3D coordinates within the 3D coordinate system, and the determining step determines when one or more footlast dimensions fits about respective foot image dimensions at the respective 3D coordinates of the 3D coordinate system.

6. The method of claim 5 further comprising the step of, storing at least one fitting representation for providing tolerances for the 3D footlast representations, anyone of the 3D footlast representations fits about the 3D foot image representation when the exterior contour is within interior contour combined with the tolerances, the tolerances combining with the interior contour to form a 3D shell representation having a thickness defined by the tolerances at respective Yn, XMn, XLn, ZIn and ZAn coordinates of the 3D coordinate system.

7. The method of claim 6 wherein, the fitting representation has respective ones of the tolerances at respective ones of the coordinates of the 3D coordinate system, the tolerances defining the thickness of the shell as a range between two tolerance values either one of which may be a positive clearance value or a negative interference value.

8. The method of claim 6 further comprising the step of, grouping contiguous coordinates of the 3D coordinate system in to one or more groups of contiguous coordinates as comfort zones, the tolerances for each respective coordinate within a comfort zone having identical tolerance values.

9. The method of claim 6 wherein, the 3D footlast representation is in compressed form having a dimensional data representing more than one dimensions for a respective more than one of the coordinates of the 3D coordinate system.

10. The method of claim 1 further comprising the step of, determining a best fitting acceptable 3D footlast representation of the 3D footlast representations determined acceptable during the acceptable determining step.

11. The method of claim 10 wherein, the 3D foot image representation provides foot image dimensions referenced to respective 3D coordinates, the foot image representation has length dimensions for respective Yn coordinates, medial width dimensions for respective XMn coordinates, lateral width dimensions for respective XLn coordinates, instep height dimensions for respective ZIn coordinates and arch height dimensions for respective ZAn coordinates, the Yn, XMn, XLn, ZIn and ZAn coordinates forming a 3D coordinate system, the 3D footlast representations provide footlast dimensions referenced to the respective 3D coordinates within the 3D coordinate system, and the acceptable determining step determines when one or more foot image dimensions fits about respective footlast dimensions at respective ones of the 3D coordinates of the 3D coordinate system, the method further comprising the step of, storing at least one fitting representation for providing tolerances of the 3D footlast representations, anyone of the 3D footlast representations fits about the 3D foot image representation when the exterior contour is within interior contour combined with the tolerances, the tolerances combining with the interior contour to form a 3D shell representation having a thickness defined by the tolerances at respective Yn, XMn, XLn, ZIn and ZAn coordinates of the 3D coordinate system, the best determining step determining for one or more of the coordinates one or more respective coordinate values representing an extent to which one or more respective ones of the foot image dimensions extends into the 3D shell, the best fit being determined by one of the acceptable 3D footlast representations with a greatest number of acceptable coordinate values.

12. The method of claim 11 wherein, the fitting storing step further stores fitting weights in the fitting representation for each of the one or more coordinates of the 3D coordinate system, and the fitting weights weigh the coordinate values, the best determining step sums the weighted coordinate values into a best fit value for each of the acceptable 3D footlast representations for determining which one of the acceptable 3D footlast representations is the best fitting acceptable 3D footlast representation.

13. The method of claim 12 wherein, the coordinate values are zero for poor acceptable fits and one for good acceptable fits, and the fitting weights are in a range from one to ten.

14. The method of claim 12 further comprising the steps of, enhancing the 3D foot image representation with a ball tab representation that abruptly changes the exterior contour only at a ball location of the human foot of the 3D foot image representation, and enhancing the 3D footlast representation with a bend tab representation that abruptly changes the interior contour only at a bend location of the 3D footlast representation, the acceptable determining step determining that a 3D footlast representation is acceptable when the ball location is aligned with the bend location.

15. A method for determining an acceptable fit of a desired style of footware in reference to footlasts defining respective sizes of the desired style of footware, the method comprising the steps of, storing a three dimensional (3D) foot image representation defining an exterior contour of a human foot, storing respective 3D footlast representations defining respective interior contours of the footlasts, determining which one or more of the footlasts has an acceptable fit when one or more respective ones of the interior contours fits about the exterior contour, imaging a human foot for generating the 3D foot image representation, referencing the 3D foot image to identify the human foot, receiving the 3D foot image representation referenced to the human foot identification, receiving a request for the desired style referenced to a style identification and referenced to the human foot identification, referencing a footlast determined to be acceptable to a footlast identification indicating one of the sizes, communicating footlast identification for indicating an acceptable size of the desired style of footware.

16. The method of claim 15 further comprising the steps of, referencing the style identification to a manufacturer identification for identifying a source of the footware, and referencing the footlast identifications style identification, and storing the manufacturer identification, style identification, and footlast identification in a footware database within a footware data structure for cross referencing the desired style to the manufacturer and to the footlasts for identifying the 3D footlast representations of the desired styled upon reception of the request.

17. The method of claim 16 further comprising the steps of storing at least one fitting representation for providing tolerances of the 3D footlast representations, one of the 3D footlast representations fits about the 3D foot image representation when the exterior contour is within interior contour combined with the tolerances, referencing fitting identification of the at least one fitting representation to the footlasts of the desired style, and storing the fitting identification in the footware database within the footware data structure for cross referencing the fitting identification to the footlasts of the desired style for determining the acceptable fit of one of the 3D footlast representations.

* * * * *